United States Patent [19]

La Croix et al.

[11] Patent Number: 5,962,432
[45] Date of Patent: Oct. 5, 1999

[54] STERILIZED, ISOTONIC AND PH-ADJUSTED PHARMACEUTICAL FORMULATION OF URIDINE TRIPHOSPHATE

[75] Inventors: Karol La Croix, Cary; Christy Shaffer, Chapel Hill; Karla Jacobus, Cary; Janet Rideout, Raleigh; David Drutz, Chapel Hill, all of N.C.

[73] Assignee: Inspire Pharmaceuticals, Inc., Durham, N.C.

[21] Appl. No.: 08/675,555

[22] Filed: Jul. 3, 1996

[51] Int. Cl.$^6$ ................................................... A61K 31/70
[52] U.S. Cl. .............................................. 514/47; 514/45
[58] Field of Search ........................................ 514/47, 45

[56] References Cited

U.S. PATENT DOCUMENTS 5,292,498  3/1994  Boucher, Jr. .
5,420,116  5/1995  Puchelle et al. .

FOREIGN PATENT DOCUMENTS 597360  3/1961  Belgium .

OTHER PUBLICATIONS

WPIDS00325F (1993).
R. Boucher, et al, Adenosine and Adenine Nucleotides: From Molecular Biology to Integrative Physiology, pp. 525–532 entitled "Mechanisms and Therapeutic Actions of Uridine Triphosphates in the Lung" (L. Belardinelli, et al. ed., Alumwer Academic Publishers, Boston 1995).

P. Noone, et al., abstract submitted to the 1996 International Conference of The American Thoracic Society.

D. Hoard and D. Ott, *J. Am. Chem. Soc.* 87, 1785–88 (1965).

M. Yoshikawa, et al., *Tetrahedron Lett.* 5056–68 (1967) and idem, *Bull. Chem. Soc.*83, 649–59 (1961).

B. Fischer, et al., *J. Med. Chem.* 36, 3937–46 (1993).

*Primary Examiner*—Zohreh Fay
*Attorney, Agent, or Firm*—Albert P. Hallulin; John A. Bendrick; Howrey & Simon

[57] ABSTRACT

A novel formulation of uridine 5'-triphosphate (UTP) for use in promoting increased mucociliary clearance of retained mucous secretions of the human airways, middle/inner ears, or sinuses is disclosed. The composition comprises UTP and aqueous solution having a therapeutic concentration between 5 and 35 mg/mL, which has controlled tonicity within the range of 250 to 1000 mOsM, pH-adjusted, having pH between 7.0 and 7.5; and sterile. The pH-adjusted formulation is capable of long-term storage in the refrigerated state, with a shelf life of up to 30 months if kept refrigerated at 5° C. The formulation is delivered therapeutically either in a nebulized form using any of several commercially available nebulizers (e.g., jet, ultrasonic, etc.), or in liquid form.

5 Claims, No Drawings

STERILIZED, ISOTONIC AND PH-ADJUSTED PHARMACEUTICAL FORMULATION OF URIDINE TRIPHOSPHATE

INTRODUCTION

1. Technical Field

This invention relates to a novel pharmaceutical formulation of uridine 5'-triphosphate (UTP) which is sterilized, of controlled tonicity and pH-adjusted for the purpose of promoting mucociliary clearance of retained mucous secretions by hydrating the secretions and stimulating ciliary beat frequency in the human airways, middle/inner ears, or sinuses. The formulation is capable of both therapeutic and diagnostic applications.

2. Background of the Invention

Mucociliary clearance is an important defense mechanism of the human airways and middle/inner ear tract. Coordinated beats of cilia in the nose, trachea, bronchi, sinuses and middle ears propel the mucous layer toward the pharynx, carrying along with it microorganisms and other particles captured in the mucus. Normal function of this system depends on the frequency and coordination of ciliary beating and the properties of the mucus itself.

It has been discovered that extracellular nucleoside triphosphates, especially UTP, modulate mucociliary clearance. Specifically, UTP stimulates ciliary beat frequency and increases hydration of the mucous layer on the luminal surface of the airway. (R. Boucher, et al., Adenosine and Adenine Nucleotides: From Molecular Biology to Integrative Physiology, p. 525–32 entitled "Mechanisms and Therapeutic Actions of Uridine Triphosphates in the Lung" (L. Belardinelli, et al. ed., Alumwer Academic Publishers, Boston 1995)). It has been postulated that UTP is effective in the treatment of cystic fibrosis and other airway diseases involving retained mucous secretions as described in U.S. Pat. No. 5,292,498 and U.S. Pat. No. 5,420,116 (applicant intends the disclosure of this and all other patent references and publications cited herein be incorporated herein by reference). It has also been demonstrated that UTP is safe and improves cough clearance in PCD patients. (P. Noone, et al., abstract submitted to the 1996 International Conference of The American Thoracic Society). Inspire Pharmaceuticals, Inc. (Durham, N.C.) has also postulated that UTP will help induce a sputum sample by hydrating mucous secretions and stimulating ciliary beat frequency for diagnostic analysis, such as cytopathology for lung cancer or AFB for tuberculosis.

With the prospect of increasing clinical use on the horizon, the need for a more bio-compatible UTP formulation has emerged. A UTP formulation under the tradename Uteplex® is marketed in France by Wyeth for the treatment of lower back pain. It has a pH of 9.0. The French biotechnology company Synthelabo has developed a formulation of adenosine triphosphate (ATP) under the tradename rhinATP™ for the treatment of nasal mucous fluid congestion. The formulation of the present invention differs from these and other prior art nucleotide pharmaceutical formulations in that it is sterilized, at a controlled tonicity and pH-adjusted to give values in the range of 6.5 to 8.5, preferably 6.5 to 8.0, most preferably 7.0 to 7.5. An unexpected property of the present invention is that the formulation is capable of extended shelf-life if kept properly refrigerated. This novel UTP formulation is compatible for use in a commercially available nebulizer (e.g., jet nebulizers, ultrasonic nebulizers, etc.) which facilitate its administration in the clinical setting.

The liquid UTP formulation of the present invention can be delivered to the lungs or sinuses of a patient via inhalation of a nebulized form of the formulation, or it may be delivered to the sinuses or middle/inner ears by means of nasal, eye, ear or oral drops. In either the nebulized or liquified form, an effective amount of UTP contacts the affected site either directly or via systemic absorption and circulation.

SUMMARY OF THE INVENTION

A novel pharmaceutical composition of UTP is disclosed. The composition comprises a UTP raw material, e.g., UTPNa$_3$ dihydrate, and a sterile aqueous solution, e.g., saline solution. This novel formulation of UTP is well-suited to be therapeutically administered in the clinical setting in order to promote muciliary clearance in patients suffering from retained mucous secretions in the lungs, sinuses or middle/inner ears, to induce sputum for puposes of diagnostic analysis, to clear the lungs of various airborne toxins, to clear the lungs prior to radiological imaging, and to clear the lungs prior to vaccination or gene therapy. This formulation of UTP is an advancement over the prior art in that it is sterilized, pH-adjusted, of controlled tonicity, and capable of extended shelf life when kept properly refrigerated. This formulation is compatible for use in a variety of commercially available nebulizers (such as jet or ultrasonic nebulizers). The formulation also encompasses the pharmaceutically acceptable salts of UTP, e.g., an alkali metal salt such as sodium or potassium; an alkaline earth salt; or an ammonium or tetraalkyl ammonium salt (i.e., NX$_4^+$ wherein X is C$_{1-4}$).

Because UTP is somewhat heat labile, the formulation of the present invention is sterilized by filtration rather than heat.

A second aspect of the present invention is that the tonicity can be controlled, e.g., for an isotonic formulation, UTPNa$_3$ is dissolved in the appropriate amount of saline or other aqueous solution to control tonicity within the osmolarity range of 250 to 1000 mOsM; the preferred osmolarity level is between 250 to 450 mOsM; the most preferred osmolarity is approximately 300 mOsM, i.e., an isotonic solution.

A third aspect of the present invention is that the formulation is pH-adjusted to be in the range of 6.0 to 8.5; the preferred pH level is between 7.0 and 7.5.

A fourth aspect of the present invention is that it may be formulated in multiple concentrations of UTP between 0.1 and 100 mg/mL; the preferred therapeutic UTP concentration is between 5 and 35 mg/mL.

A fifth, and unexpected, aspect of the present invention is that a formulation with a pH value of 7.0 to 7.5 will remain in stable form for up to 30 months when stored at a temperature between 0° to 10° C. The preferred storage temperature is 5° C.

DESCRIPTION OF THE SPECIFIC EMBODIMENT

The composition of the present invention is a novel formulation of UTP and sterile aqueous solution which is well-suited for clinical therapeutic administration because it is sterilized, has a controlled tonicity, is pH-adjusted, and is compatible for administration in a variety of commercially available nebulizers (such as jet or ultrasonic). An unexpected property of the present invention is that it is capable of extended shelf-life when stored in a refrigerated state. Its therapeutic purpose is to increase mucociliary clearance of retained mucous secretions from the lungs, sinuses and middle/inner ears of patients suffering from cystic fibrosis, bronchitis, sinusitis, otitis media, primary ciliary dyskinesia, ventilator-associated pneumonia and other diseases involved retained mucous secretions or impaired ciliary movement, as well as bedridden individuals not suffering from any diseases but who have a high risk of accumulating mucous secretions, e.g., quadriplegics. The formulation also helps induce sputum samples for diagnostic analysis, e.g., for diagnosis of lung cancer, tuberculosis or other lung diseases.

The formulation of the present invention is primarily intended for administration to a human subject, but may also be administered to other mammalian subjects, such as dogs and cats, for veterinary purposes.

Additionally, because of the well-demonstrated ability of the active compound of the present formulation to enhance lung mucociliary clearance in normal subjects, the formulation of the present invention may be used to accelerate the clearance of any type of inhaled foreign material from the airways. This would prove beneficial in a number of situations, e.g., biological warfare; smoke inhalation; industrial and mining exposure to inhaled toxins (resulting in silicosis, anthracosis and the gamut of so-called pneumoconioses); and allergic reaction to inhaled particles such as pollen.

The formulation may be administered to the lungs or sinuses in a nebulized form which the patient inhales, or it may be administered to the sinuses or ears in a liquid form, i.e., nose, eye or ear drops. With either the nebulized or liquid form, an effective amount of UTP contacts the affected site either directly or via systemic absorption and circulation.

The formulation of the present invention also encompasses the pharmaceutically acceptable salts of UTP, e.g., an alkali metal salt such as sodium or potassium; an alkaline earth salt, or an ammonium or tetraalkyl ammonium salt (i.e., $NX_4^+$ wherein X is $C_{1-4}$). Pharmaceutically acceptable salts are salts that retain the desired biological activity of the parent compound and do not impart undesired toxicological effects.

The raw material for the formulation of the present invention—e.g., $UTPNa_3$ dihydrate, can be made in accordance with known procedures or variations thereof which will be apparent to those skilled in the art. For example, phosphorylation of nucleosides can be accomplished by standard methods such as D. Hoard and D. Ott, *J. Am. Chem. Soc.* 87, 1785–88 (1965); M. Yoshikawa, et al., *Tetrahedron Lett.* 5065–68 (1967) and *idem, Bull. Chem. Soc.* 83, 649–59 (1961); and B. Fischer, et al., *J. Med. Chem.* 36, 3937–46 (1993) and references therein. In addition, UTP is commercially available.

The UTP in powder form must be kept frozen at a temperature between −20° C. and −80° C., and should not be allowed to warm to room temperature for more than one hour prior to the formulation procedure. Additionally, the UTP raw material should be brought to handling temperature before opening to minimize water absorption.

The tonicity of the liquid formulation of the present invention can be controlled by adding a sterile aqueous solution, e.g., saline solution, to dry powder $UTPNa_3$ by techniques known to those skilled in the art to bring the tonicity to any desired level of osmolarity within the range of 250 to 1000 mOsM; preferably, the osmolarity of the solution is within the range of 250 to 450 mOsM; most preferably, the solution is isotonic with biologic fluids, i.e., the osmolarity is approximately 300 mOsM. The solution is pH adjusted by techniques known to those skilled in the art such that the pH of said solution is between 6.0 and 8.5; preferably the pH is between 7.0 and 7.5. The solution is then sterilized by filtration using an appropriate micron filter.

An unexpected result of the present invention is that this isotonic, pH-adjusted and sterilized formulation of UTP will remain in stable form for up to 30 months if stored at a temperature between 0° to 10° C. Because previous UTP formulations had to be stored in frozen form, the formulation of the present invention also confers a practical benefit—valuable freezer space is freed up.

The present invention can be formulated at multiple concentrations of UTP between 0.1 and 100 mg/mL; the preferred therapeutic concentration of UTP is between 5 and 35 mg/mL.

Clinical administration of the formulation of the present invention is facilitated because it is suitable for administration utilizing most commercially available nebulizers, e.g., the Pari LC Plus jet nebulizer.

The present invention is explained in greater detail in the Example which follows. This example is intended as illustrative of the invention, and is not to be taken as limiting thereof.

EXPERIMENTAL

Example 1

Preparation of a 6-Liter Pilot GMP Batch

Prior to formulation, $UTPNa_3$ dihydrate is kept frozen at −20° C. The UTP powder is allowed to warm to handling temperature for at least one hour prior to opening; this is to minimize water absorption. The UTP raw material is dissolved in sterile aqueous solution, e.g., saline solution. An appropriate concentration of saline solution is used to bring the osmolarity to approximately 300 mOsM, i.e., an isotonic solution. Alternatively, UTP powder can be dissolved in sterile water and an appropriate amount of NaCl is added to bring the osmolarity to approximately 300 mOsM. In either case, aqueous solution is added in sufficient volume to reach an optimum therapeutic UTP concentration level of 5 to 35 mg/mL. The liquid solution is pH-adjusted to bring the pH level to between 7.0 and 7.5. The resulting UTP solution is sterilized by filtration with an appropriate micron filter.

The following quality control tests are then performed prior to packaging: bacteriostasis/fungistasis; endotoxin assay; high-pressure liquid chromatography, osmolarity assay; pH-level assay; concentration assay; and visual inspection for any particulate matter. Any rejected vials are destroyed.

Approximately 1250 vial containers are then filled per 6-liter batch to a level of 4.2 mL to 4.6 mL each, with a fill target of 4.4 mL (the label claim is 4.0 mL). Vials are shipped within two weeks of manufacture.

What is claimed is:

1. A sterile pharmacutical composition comprising uridine 5'-triphosphate and sterile aqueous solution having a concentration of uridine 5'-triphosphate sufficient to provide between 21 mg to 161 mg of uridine 5'-triphosphate per dosage; an osmolarity value between 250 and 450 mOsM; a pH level between 6.0 and 8.5; and an acceptable sterility level.

2. A solution according to claim 1 which is isotonic, with an osmolarity of approximately 300 mOsM.

3. A solution according to claim 1 in which the pH is between 7.0 and 7.7.

4. A solution according to claim 1 which is administered to a patient in need thereof by inhalation.

5. A solution according to claim 1 which remains stable at temperatures between 0°–10° for up to 30 months.

* * * * *